(12) United States Patent
Weaver, II et al.

(10) Patent No.: US 8,622,947 B2
(45) Date of Patent: Jan. 7, 2014

(54) ANKLE SUPPORT WITH SPLINT AND METHOD OF USING SAME

(75) Inventors: Edward L. Weaver, II, Milford, OH (US); John R. Elrod, Cincinnati, OH (US)

(73) Assignee: 3M Innovative Properties Company, Saint Paul, MN (US)

( * ) Notice: Subject to any disclaimer, the term of this patent is extended or adjusted under 35 U.S.C. 154(b) by 317 days.

(21) Appl. No.: 12/992,307

(22) PCT Filed: May 8, 2009

(86) PCT No.: PCT/US2009/043310
§ 371 (c)(1),
(2), (4) Date: Mar. 3, 2011

(87) PCT Pub. No.: WO2009/140165
PCT Pub. Date: Nov. 19, 2009

(65) Prior Publication Data
US 2011/0144554 A1    Jun. 16, 2011

Related U.S. Application Data

(60) Provisional application No. 61/127,604, filed on May 14, 2008.

(51) Int. Cl.
*A61F 5/00*      (2006.01)
(52) U.S. Cl.
USPC ............................................................ 602/27
(58) Field of Classification Search
USPC .............. 602/27, 23, 5, 1, 6, 7, 40, 60–62, 65
See application file for complete search history.

(56) References Cited

U.S. PATENT DOCUMENTS

| 851,950 | A | | 4/1907 | Le Mat |
| 1,027,897 | A | | 5/1912 | Quenzer |
| 1,037,441 | A | | 9/1912 | Collis |
| 1,081,366 | A | | 12/1913 | Collis |
| 2,800,900 | A | * | 7/1957 | Schultz ........................ 602/27 |
| 3,028,861 | A | | 4/1962 | Shapiro |

(Continued)

FOREIGN PATENT DOCUMENTS

| CN | 2033672 | 3/1989 |
| CN | 2600076 | 1/2004 |

(Continued)

OTHER PUBLICATIONS

Intl Search Report for PCT/US2009/043310, 4 pages.

(Continued)

*Primary Examiner* — Patricia Bianco
*Assistant Examiner* — Tarla Patel
(74) *Attorney, Agent, or Firm* — Kevin W. Weber (57) ABSTRACT

According to one embodiment, an orthopedic support for supporting a portion of a wearer's anatomy is provided. For example, the orthopedic support may be an ankle brace comprising a sheet of flexible material configured to at least partially enclose a wearer's ankle and a splint coupled to the sheet of material. The splint is configured to be positioned on a medial side of the wearer's ankle when the sheet of material is secured on the wearer's ankle and includes an undulating profile configured to conform to at least a portion of the medial side of the wearer's ankle and resist inversion of the ankle.

16 Claims, 6 Drawing Sheets

(56) References Cited

U.S. PATENT DOCUMENTS

| | | | |
|---|---|---|---|
| 3,298,365 | A | 1/1967 | Lewis |
| 3,970,083 | A | 7/1976 | Carrigan |
| 4,187,844 | A | 2/1980 | Caprio, Jr. |
| 4,237,874 | A | 12/1980 | Nelson |
| 4,280,488 | A | 7/1981 | Polsky |
| 4,527,556 | A | 7/1985 | Nelson |
| 4,651,726 | A | 3/1987 | Holland |
| 4,724,847 | A | 2/1988 | Nelson |
| 4,825,856 | A | 5/1989 | Nelson |
| 4,878,504 | A | 11/1989 | Nelson |
| 4,936,295 | A | 6/1990 | Crane |
| 4,960,135 | A | 10/1990 | Nelson |
| 5,000,195 | A | 3/1991 | Neal |
| 5,007,417 | A | 4/1991 | Bender |
| 5,014,691 | A | 5/1991 | Cueman |
| 5,078,128 | A | 1/1992 | Grim |
| 5,630,792 | A | 5/1997 | Neal |
| 5,657,767 | A | 8/1997 | Nelson |
| 5,681,271 | A | 10/1997 | Nelson |
| D388,173 | S | 12/1997 | Eriksson |
| 5,741,222 | A * | 4/1998 | Fiore ................. 602/27 |
| D394,112 | S | 5/1998 | Duback |
| 5,795,316 | A | 8/1998 | Gaylord |
| 5,853,381 | A | 12/1998 | Stevenson |
| 5,868,693 | A | 2/1999 | Duback |
| 5,944,678 | A | 8/1999 | Hubbard |
| 6,155,997 | A | 12/2000 | Castro |
| 6,394,971 | B1 | 5/2002 | Slautterback |
| 6,398,750 | B1 | 6/2002 | Quinn |
| 6,540,705 | B2 | 4/2003 | Norstrem |
| 6,602,215 | B1 | 8/2003 | Richie, Jr. |
| 6,652,474 | B1 | 11/2003 | Quinn |
| 6,663,583 | B1 | 12/2003 | Janis |
| 7,014,621 | B2 | 3/2006 | Nelson |
| D552,744 | S | 10/2007 | Verkade |
| 7,497,839 | B2 | 3/2009 | Quinn |
| 7,651,472 | B2 | 1/2010 | Gaylord |
| D639,965 | S | 6/2011 | Wehsely-Swiczinsky |
| D649,651 | S | 11/2011 | Weaver |
| 2002/0095750 | A1 | 7/2002 | Hammerslag |
| 2003/0233062 | A1 * | 12/2003 | McCormick et al. ........... 602/65 |
| 2005/0165338 | A1 | 7/2005 | Iglesias |
| 2005/0273025 | A1 * | 12/2005 | Houser ......................... 602/16 |
| 2006/0004310 | A1 | 1/2006 | Parizot |
| 2006/0004311 | A1 | 1/2006 | Hargrave |
| 2006/0052734 | A1 | 3/2006 | Evans |
| 2006/0156517 | A1 | 7/2006 | Hammerslag |
| 2007/0167895 | A1 * | 7/2007 | Gramza et al. ................. 602/26 |
| 2007/0169378 | A1 | 7/2007 | Sodeberg |
| 2008/0066272 | A1 | 3/2008 | Hammerslag |

FOREIGN PATENT DOCUMENTS

| | | |
|---|---|---|
| EP | 820741 | 1/1998 |
| JP | 3072845 | 11/2000 |
| KR | 10-2007-0078568 | 8/2007 |
| WO | 92/18072 | 10/1992 |
| WO | WO 2005/087150 A1 | 9/2005 |
| WO | WO 2007-051524 | 5/2007 |
| WO | WO 2010-117723 | 10/2010 |
| WO | WO 2010-117749 | 10/2010 |

OTHER PUBLICATIONS

International Search Report for PCT/US2009/043310, 4 pages.

* cited by examiner

ANKLE SUPPORT WITH SPLINT AND METHOD OF USING SAME

CROSS REFERENCE TO RELATED APPLICATIONS

This application is a national stage filing under 35 U.S.C. 371 of PCT/US2009/043310, filed May 8, 2009, which claims priority to Provisional Application No. 61/127,604, filed May 14, 2008, the disclosure of which is incorporated by reference in its/their entirety herein.

BACKGROUND OF THE INVENTION

1. Field of the Invention

The present invention is related to the field of orthopedic supports, and more particularly, to orthopedic supports having a splint for supporting a portion of a wearer's anatomy.

2. Description of Related Art

Stays or splints are commonly employed with orthopedic supports to stabilize or immobilize a joint of a wearer. Splints may be rigid for providing more support or relatively flexible for providing mobility, and frequently splints are used to support the medial and lateral sides of the joint. For instance, the medial and lateral sides of the ankle or knee commonly need to be supported due to the frequent injuries incurred from lateral forces applied to the joint. Splints may be utilized to prevent injury of a joint or to rehabilitate a joint caused by a prior injury.

Splints may be configured to provide varying degrees of support depending on the severity of the injury and the amount of mobility desired. For instance, splints for treating less serious injuries may provide less lateral stability and, thus, more mobility. While splints may be used to provide lateral stability, too much stability may sacrifice comfort and mobility for the wearer. In particular, supports that are to be used in everyday activities for treating acute or less severe injuries should provide moderate support while allowing the wearer to participate in activities without discomfort.

It would therefore be advantageous to provide an orthopedic support that imparts increased comfort and/or support for the wearer without sacrificing mobility. In addition, it would be advantageous to provide an orthopedic support that includes a splint that may be easily manufactured and used for various orthopedic applications. Moreover, it would be advantageous to provide an orthopedic support that may be secured at a desired tension to achieve a desired amount of support.

BRIEF SUMMARY OF THE INVENTION

The above and other needs may be met by embodiments of the present invention which, in one embodiment, provides an orthopedic support for supporting a portion of a limb of the wearer. The orthopedic support generally includes a sheet of flexible material for conforming to a portion of the wearer's anatomy. The orthopedic support could be utilized for supporting a variety of limbs or portions of limbs, such as the wrist, knee, elbow, or ankle of a wearer. For example, an ankle support may be provided that includes a splint configured to be positioned on a medial side of the wearer's ankle. Thus, the splint may be configured to resist inversion of the ankle, which may prevent ankle injuries such as sprains. Surprisingly, no splint is necessary on the lateral side of the wearer's ankle. The ankle support may be ambidextrous and include an adjustable tension system coupled to the sheet of material.

According to one embodiment, the splint has an undulating profile configured to conform to the wearer's calf, medial malleolus/subcutaneous bursa, and arch. Thus, the splint may have respective curvatures for conforming to each of the calf, medial malleolus/subcutaneous bursa, and the arch. The portion of the splint configured to conform to the arch may have varying configurations. For example, the end of the splint may be tapered. Or, the splint may have a hinged portion that is configured to provide rotation for facilitating flexion of the wearer's ankle.

The splint may include a cushioning material, such as a gel, foam, air bladder, or beading configured to be oriented towards the wearer during use. The cushioning material may be applied to the splint or integrally defined on the splint. For example, a polymeric splint may be formed by injection molding and have different materials of varying durometer.

The splint may be secured to the sheet of material using various fastening techniques, such as hook and loop fasteners, straps, buckles, and the like. In another variation, a strapping system may be integrated with a tension system for the sheet of material. For example, the strapping system may include one or more straps having J-hooks at each of its free ends that are configured to engage a tension system such that tightening of the tension system results in tightening of the straps. Alternatively, the splint may be inserted within a pocket defined between sheets of material. The pocket may be located on an inner surface of the sheet of material and include an opening or slit for receiving the splint. There may be a pair of pockets on the sheet of material such that the splint may be interchangeable for ambidextrous use.

According to additional aspects, the orthopedic support may include an adjustable tension system that is coupled to the sheet of material and configured to secure the sheet of material about the portion of the wearer's anatomy. For instance, the adjustable tension system may be configured to tension the sheet of material so as to draw a pair of opposing lateral edges towards one another. In addition, the adjustable tension system may be located at any desired position when the orthopedic support is worn, such as a dorsal, palmar, medial, lateral, posterior, or anterior portion of the wearer's anatomy. Furthermore, the orthopedic support may include one or more adjustable tension systems.

According to one embodiment of the present invention, the adjustable tension system includes a tightening mechanism comprising a spool and a cable coupled to the spool and the sheet of flexible material. The tightening mechanism may be configured to rotate the spool such that rotation in a first direction winds the cable about the spool so as to increase tension in the cable and secure the sheet of flexible material on the portion of the wearer's anatomy. The orthopedic support may include a plurality of guides for guiding the cable between the lateral edges of the sheet of material. The adjustable tension system may also include a release mechanism configured to disengage the spool so as to allow rotation of the spool in a second opposite direction to unwind the cable from the spool and decrease tension in the cable.

Embodiments of the present invention may provide many advantages. For instance, the orthopedic support may be an ankle support capable of being used during everyday activities and for treatment of acute ankle injuries. The ankle support may include a splint that is configured to be positioned on only a medial side of the ankle and prevent inversion that may lead to ankle injuries. In particular, the curvature of the ankle support is configured to conform to the ankle so as to provide comfort, while at the same time providing support and resistance to inversion. Moreover, the splint may be ambidextrous and may be used on the medial sides of both the left and right ankles. The ankle support may incorporate an adjustable tension system that allows a wearer to achieve a desired level of support. In addition, the ankle support may include a strapping system or pocket to facilitate positioning of the splint adjacent to the wearer's ankle.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION OF THE INVENTION

The present invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

Generally, the present invention provides an orthopedic support that includes a sheet of flexible material for wrapping about and conforming to a portion of a wearer's anatomy. The orthopedic support includes a splint configured to provide lateral stability for supporting the wearer's joint. In addition, the orthopedic support may include an adjustable tension system for securing the orthopedic support on a wearer's limb. Although reference is made to an ankle support below, the orthopedic support could be adapted for use on various limbs or portions of a limb of a wearer, such as, for example, on a wrist, knee, ankle, or elbow, back.

Figures 1A, 1B:
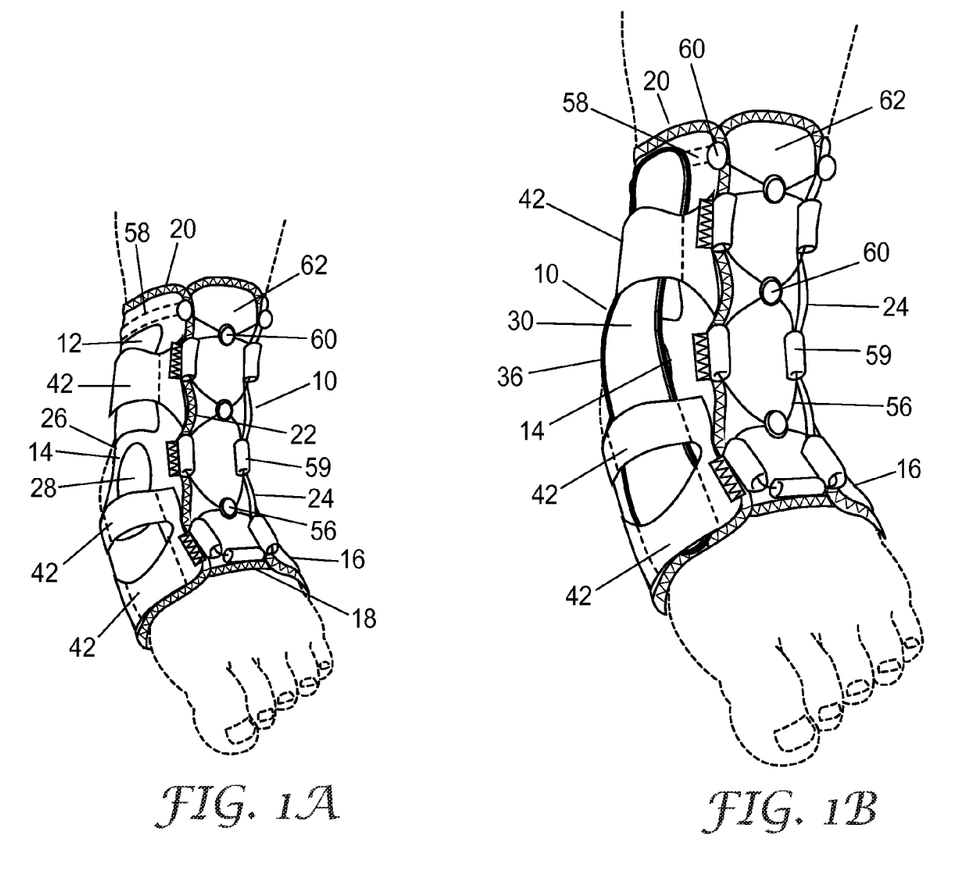
FIGS. 1A-1B illustrate anterior/medial perspective views of an ankle brace positioned on a left ankle according to one embodiment of the present invention.

With reference to FIGS. 1A and 1B, an ankle support 10 according to one embodiment of the present invention is shown. In general, the ankle support 10 includes a sheet of material 12 that is configured to extend about portions of the wearer's foot and lower leg to enclose the wearer's ankle. The sheet of material 12 may be any number of materials, such as a flexible and soft laminate material that provides moisture wicking and cushioning properties. For example, the laminate material could be a laminate of polyester, polyurethane foam, and polyester. Moreover, the sheet of material 12 may be a combination of materials, such as soft breathable material for positioning adjacent to the wearer's skin and less flexible material for providing support or reinforcement. Although the sheet of material 12 may be elastic, the sheet of flexible material could be inelastic or non-stretchable so as to facilitate tensioning of the ankle support 10.

The sheet of material 12 includes a medial portion 14 and a lateral portion 16 (note that the ankle support is ambidextrous and reference to the medial and lateral portions are for illustrative purposes only, as the ankle support may be worn on either the right or left ankle). The sheet of material 12 includes a distal edge 18 that is configured to provide an opening for receiving the wearer's foot and a proximal edge 20 for receiving the wearer's foot and ankle therethrough. The sheet of material 12 also includes a pair of lateral edges 22, 24 that may be drawn towards one another as the adjustable tension system 50 (not shown in FIG. 1A or 1B) applies tension to the ankle support 10. Moreover, the ankle support 10 could include a connector sheet 62 or tongue configured to extend at least partially between the lateral edges 22, 24. The connector sheet 62 may be attached along a portion or the entire length of the lateral edges 22, 24. Moreover, the sheet of material 12 may also include a heel opening 26 for receiving the wearer's heel and/or malleolus openings 28 for receiving the medial and lateral malleolus.

Figure 3:
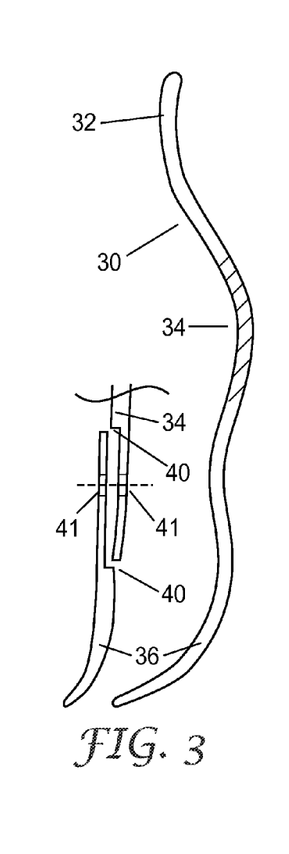
FIG. 3 is a side view of a splint according to one embodiment of the present invention.

According to the embodiment shown in FIG. 1B, the ankle support 10 further includes a splint 30 coupled to the sheet of material 12 for providing stability. The splint 30 is positioned on the medial portion 14 of the sheet of material 12. The splint 30 has an undulating profile between its proximal and distal ends for conforming to the ankle joint. For instance, FIG. 3 shows that the splint 30 includes a first portion 32 having a convex curvature for conforming to the calf, a second portion 34 having a concave curvature for conforming to the medial malleolus and subcutaneous bursa, and a third portion 36 having a concave curvature for conforming to the arch. The combination of the wearer's foot, leg, and splint 30 provides a generally triangular geometry that resists inversion or outward rotation of the ankle without the need for a splint on the lateral side of the wearer's ankle. Thus, the splint 30 is capable of providing increased comfort and decreased pressure on the calf, medial malleolus/subcutaneous bursa, and arch, while also preventing the ankle from inverting and potentially resulting in an ankle injury.

Figure 2A:
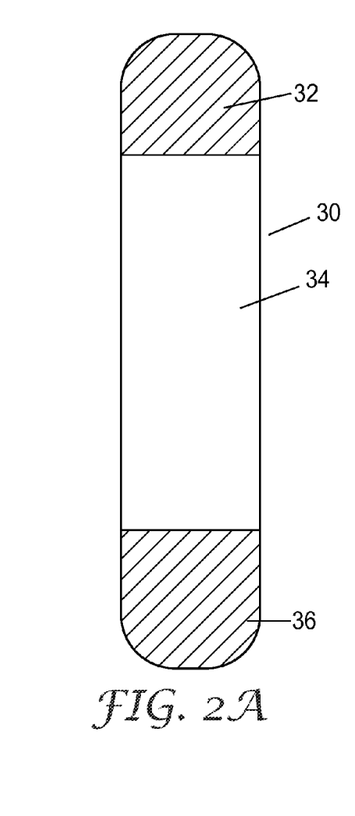
FIGS. 2A-2C are plan views of various splints according to embodiments of the present invention.
Figure 2B:
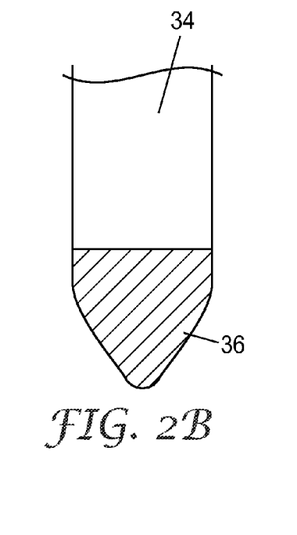

FIG. 2A demonstrates that the splint 30 may have a rectangular configuration in plan view. However, the splint 30 may have various configurations. For example, FIG. 2B shows that the third portion 36 may be tapered to decrease pressure on the arch, which may be indicated for those having pes planus or fallen arches. The splint 30 could also be curved rather than rectangular along its length, such by as having a slight curvature at its distal end.

Figure 2C:
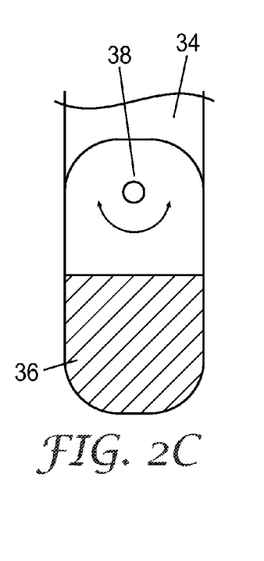

Moreover, FIG. 2C shows that the third portion 36 may be pivotably connected to the second portion 34 at a joint or hinge 38. Thus, as the wearer's foot flexes during use, the third portion 36 pivots at the joint 38, which may allow the wearer to have a more natural gait. The second 34 and third 36 portions may be configured to pivot to various angles with respect to another (e.g., 0-270°). In order to facilitate pivoting between the second 34 and third 36 portions, slots 40 may be defined in the second 34 and third 36 portions. The slots 40 may be defined such that the second 34 and third 36 portions are positioned proximate or adjacent to one another and may rotate without interference. The joint 38 could be any suitable device capable of securing the second 34 and third 36 portions together while also allowing pivoting therebetween. For instance, the joint 38 could be a rivet or similar fastener secured in holes 41 defined in the second 34 and third 36 portions.

The splint 30 may be various materials that are capable of obtaining an undulating profile and provide adequate support. For instance, the splint 30 could be a metallic (e.g., aluminum), polymeric (e.g., nylon), or composite (e.g., carbon fiber) material, as well as combinations thereof. Moreover, the splint 30 may be formed using different techniques such as injection molding or compression molding or a combination of techniques, such as punching or stamping a metallic splint and bending the splint to a desired curvature. Furthermore, the splint 30 may be various sizes for accommodating different sizes and could also be custom molded for specific wearers.

The splint 30 may include a cushioning material, such as a gel, foam, air bladder, or beading configured to be oriented towards the wearer's skin during use so as to increase the comfort and provide pressure relief. The cushioning material may be applied to the splint, such as with an adhesive, or integrally defined on the splint. For example, a polymeric splint may be formed by injection molding and have different materials of varying durometer.

The splint 30 may be secured to the sheet of material 12 using various techniques. For example, the splint 30 may be secured to the sheet of material 12 using hook and loop fasteners, straps, buckles, and the like. For example, FIGS. 1A and 1B show that a plurality of non-elastic bands may be secured to the medial portion 14 of the sheet of material 12. FIG. 1B shows that the non-elastic bands 42 are configured to receive the splint 30 and secure the splint to the sheet of material 12. Although three non-elastic bands 42 are shown, there may be any number of bands, such as two or more. Moreover, to facilitate ambidextrous use, the ankle support 10 may include non-elastic bands 42 or other securing technique on both the medial 14 and lateral 16 portions.

Figure 5A:
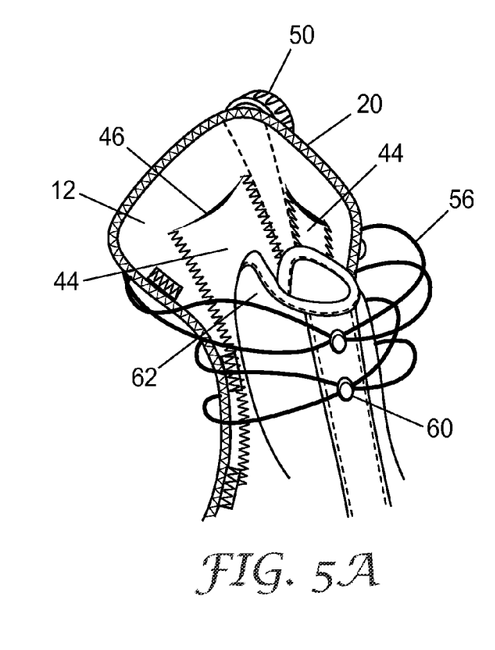
FIGS. 5A-5B are partial perspective views of an ankle support having a pocket for receiving a splint according to one embodiment of the present invention.
Figure 5B:
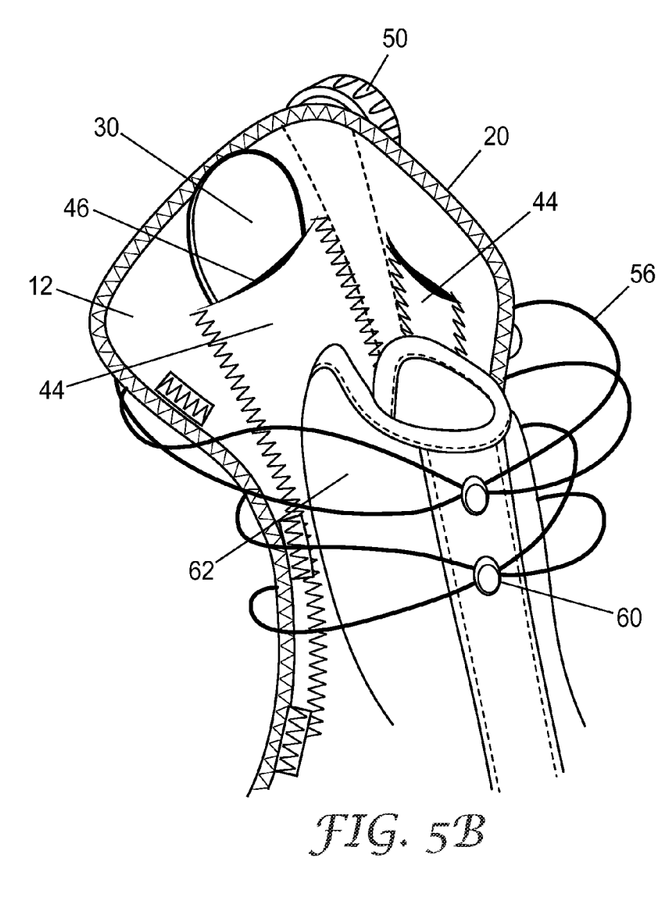

Alternatively, the splint 30 may be inserted within a pocket 44 defined between sheets of material 12, as shown in FIGS. 5A and 5B. The pocket 44 may be located on an inner surface of the sheet of material 12 and include an opening or slit 46 for receiving the splint 30. There may be a pair of pockets 44 defined between sheets of material 12 such that the splint 30 may be interchangeable for ambidextrous use as is shown in FIGS. 5A and 5B. The pocket 44 could also be defined on the outer surface of the sheet of material 12 and could be formed using various techniques, such as sewing, RF welding, or otherwise securing the pocket on the sheet of material 12. When formed between two sheets of material 12, the pocket 44 could also be sectioned off to define the pocket for receiving a splint 30 using similar techniques.

Figure 4:
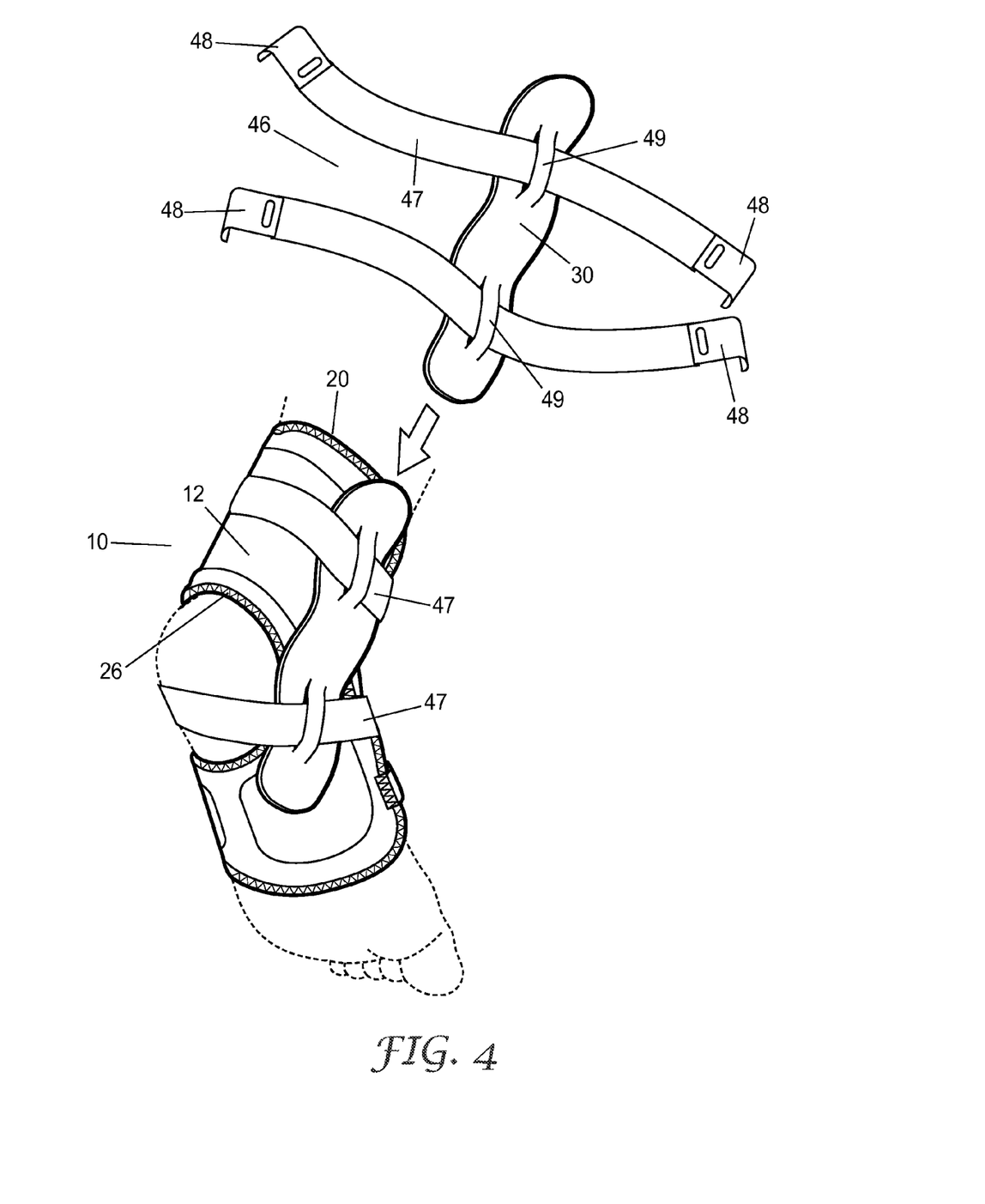
FIG. 4 is a posterior/medial perspective view of an ankle support having a strapping system according to another embodiment of the present invention.

FIG. 4 illustrates a strapping system 46 that may be used to secure the splint 30 to the sheet of material 12, according to one embodiment of the present invention. The strapping system 46 may include one or more straps 47 having hooks 48 at each of its free ends, wherein the hooks may be J-shaped. The splint 30 may have guides 49 for receiving respective straps 47. There may be any number of straps 47 employed to secure the splint 30 to the sheet of material 12, such as two or more. According to one embodiment, the strapping system 46 may be integrated with an adjustable tension system 50, which is explained in further detail below. The hooks 48 may be configured to engage the tensioning system 50 (not shown in FIG. 4) such that tightening of the tensioning system results in tightening of the straps 47, thereby securing the splint 30 to the sheet of material 12. For instance, the hooks 48 may be configured to engage a cable 56 (not shown in FIG. 4) integrated with the tension system. Thus, by adjusting the tension in the cable 56 with the tension system 50, the tension in the straps 47 also adjusts such that the wearer is able to increase or decrease the level of support provided by the splint 30.

Figure 7A:
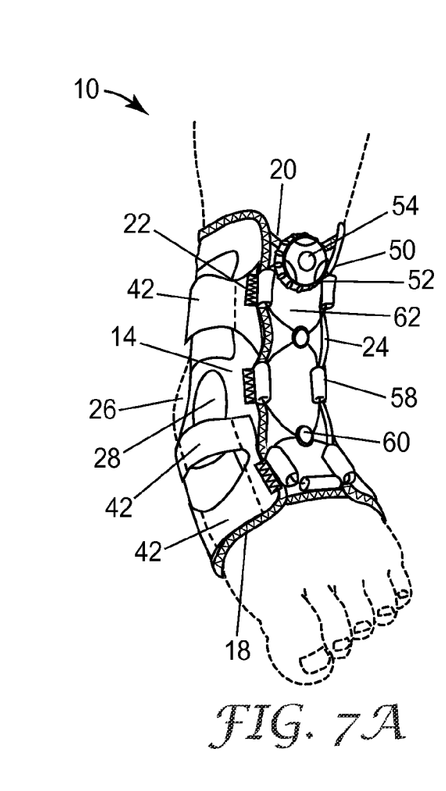
FIGS. 7A-7B are front and medial perspective views of an ankle support positioned on a left ankle according to an embodiment of the present invention.
Figure 7B:
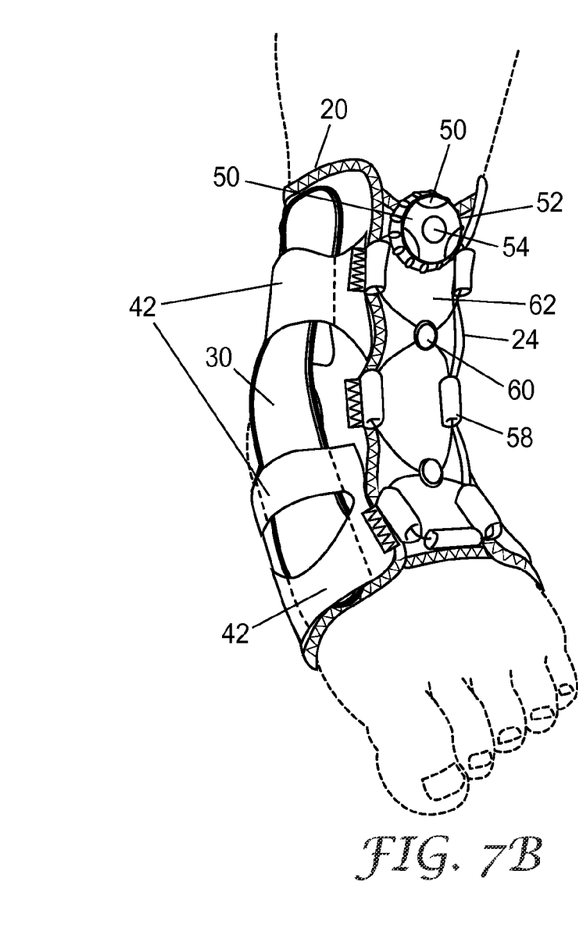

According to the embodiment shown in FIGS. 7A and 7B, the ankle support 10 includes an adjustable tension system 50 for securing the sheet of material 12 to the wearer's ankle for supporting the ankle. In general, the adjustable tension system 50 includes a tightening mechanism 52 for securing the ankle support 10 to a portion of a wearer's anatomy and a release mechanism 54 for facilitating removal of the ankle support. The adjustable tension system 50 may be used to adjust the amount of support desired by a wearer. The adjustable tension system may also maintain the ankle support 10 in a ready-to-wear configuration, such that the support may be readily positioned and secured on the wearer's ankle. Furthermore, the tension system 50 may allow the wearer to apply even tension throughout the ankle support 10.

The tightening mechanism 52 may be a thumbwheel or other mechanism that may be rotated by the wearer in a clockwise or counterclockwise direction to apply tension to the ankle support 10. For example, the tightening mechanism 52 could include a spool to wind cable 56 thereabout. The release mechanism 54 may be a spool cover or similar mechanism configured to be depressed so as to disengage the tightening mechanism, which releases tension in the cable 56. The tension in the cable 56 may cause the spool to spin freely and unwind the cable until there is no tension left in the cable. Thus, the release mechanism 54 may allow the wearer to release tension in the cable 56 wound about the spool so as to facilitate removal of the ankle support 10. It is understood that alternative release mechanisms 54 may be utilized in alternative embodiments. For example, tension in the cable 56 could be released by rotating the tightening mechanism 52 in an opposite direction than that which the cable is wound about the spool.

Alternatively, there may be two tightening mechanisms 52, one engaging a cable 56 controlling the tension of the top portion of the brace and one engaging a cable 56 controlling the tension of the bottom portion of the brace. This embodiment will allow the user to independently adjust the tension in the top and bottom portions of the brace. Both tightening mechanisms 52 may be present on the anterior or posterior portion of the brace. Alternatively, one tightening mechanism 52 may be present on the anterior and one on the posterior portion of the brace.

The cable 56 may be any suitable strand, lace, solid wire or polymer, monofilament material, or multifilament material that could be woven or braided. In addition, the cable 56 may be coated to increase its slidability and durability, such as with a polymeric coating. One or both ends of a cable 56 may be coupled to the tightening mechanism 52, and the ankle support 10 may incorporate one or more cables. Alternatively, one or both ends of the cable 56 may be coupled to the ankle support 10 and wound about the spool rather than being directly coupled to the spool.

Figure 6:
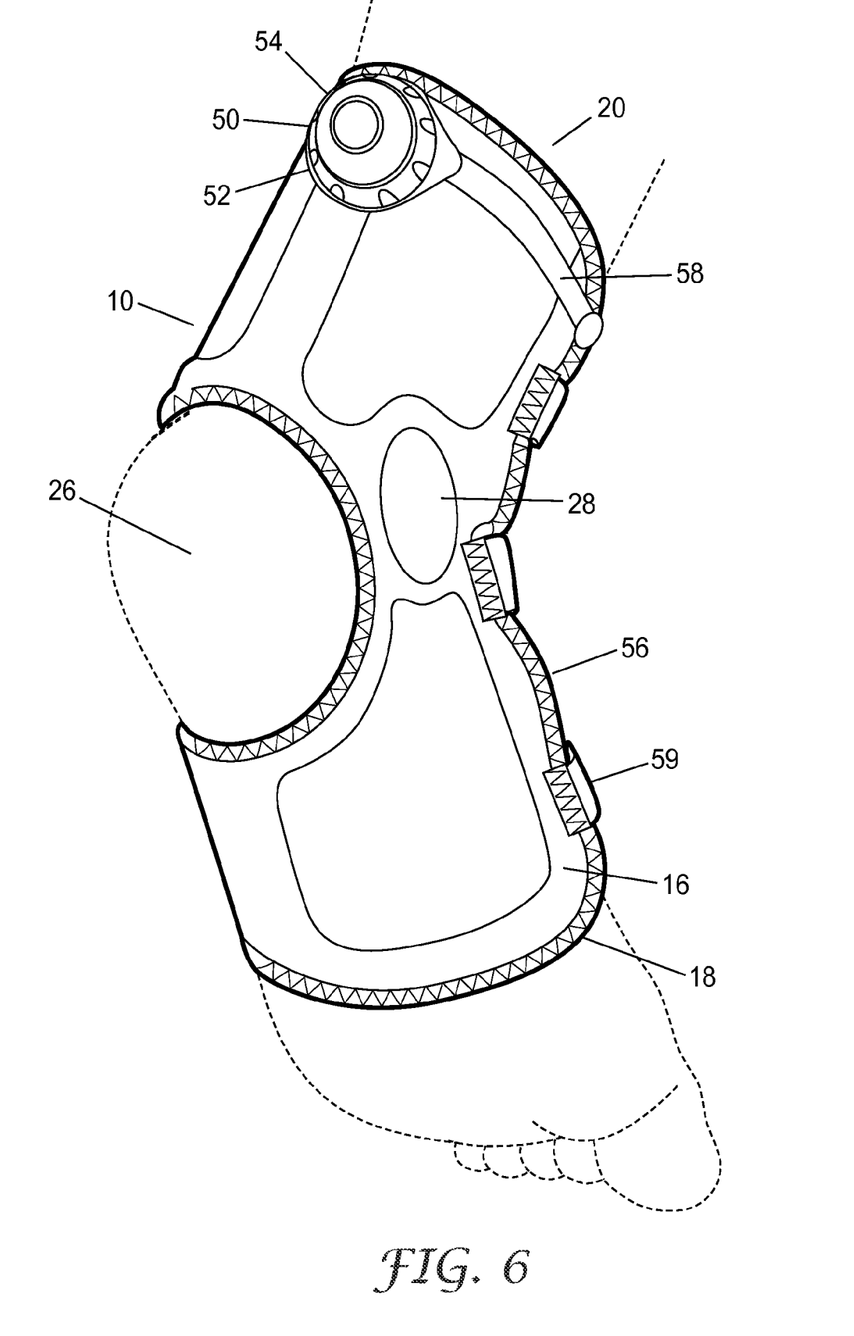
FIG. 6 is a posterior/lateral perspective view of an ankle brace positioned on a right foot according to one embodiment of the present invention.

The ankle support 10 may also include a plurality of guides 59. The guides 59 may be cylindrical and hollow as well as configured to slidably receive the cable 56 therethrough. The guides 59 may be configured to guide the cable 56 at various locations on the sheet of material 12. For instance, the guides 59 may be configured to create opposing points at one or more locations on the ankle support 10 in order to create tension in the cable 56. Thus, a series of guides 59 may be used in any desired configuration to create even tension along the ankle support 10. For example, FIGS. 7A and 7B illustrate that the guides 59 may be arranged along the lateral edges 22, 24 of the sheet of material 12 so that the cable 56 extends in a crisscross pattern on the ankle support 10. In addition, FIG. 6 shows that a circumferential guide 58 may extend about the sheet of material 12, while FIGS. 1A and 1B demonstrate that the cable 56 may extend through the sheet of material 12 or have a circumferential guide positioned within the sheet of material between an inner and outer layer. The guides 58 and 59 could be secured to the ankle support 10 using various techniques, such as by injection molding or adhering the posts directly onto the sheet of material. Furthermore, the guides 58 and 59 could be various sizes and configurations, such as hooks, loops, or the like that are configured to receive the cable 56 and guide the cable about the sheet of material 12.

According to one aspect, the ankle support 10 may include one or more cable guides 60 having an opening for receiving the cable 56 and guiding the cable between the lateral edges 22, 24. The cable guides 60 may be secured to the connector sheet 62 or may be held in position simply be threading the ends of the cable 56 therethrough.

The adjustable tension system 50 may be attached to various locations on the sheet of material 12. In FIGS. 1A, 1B, 5A, 5B, and 6, for example, the tension system 50 is positioned on a posterior portion of the sheet of material 12, while in FIGS. 7A and 7B the tension system is located on the anterior portion of the ankle support 10. The adjustable tension system 50 could be attached to any other desired location on the sheet of material 12, such as the medial 14 and/or lateral 16 portions. Moreover, the ankle support 10 could include a connector sheet 62 or tongue configured to extend at least partially between the lateral edges 22, 24, and the adjustable tension system 10 could be attached to the connector sheet, as shown in FIGS. 7A and 7B.

Many modifications and other embodiments of the invention set forth herein will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. An ankle support comprising:
a sheet of flexible material configured to at least partially enclose a wearer's ankle; and
a splint coupled to the sheet of material and configured to be positioned on a medial side of the wearer's ankle wherein splint provides a generally triangular geometry that resists inversion or outward rotation of the ankle when the sheet of material is secured on the wearer's ankle, wherein there is no splint configured to be positioned on a lateral side of the wearer's ankle when the sheet of material is secured on the wearer's ankle, and wherein the splint comprises an undulating profile configured to conform to at least a portion of the medial side of the wearer's ankle and resist inversion of the ankle, wherein the undulating profile includes a first portion having a convex curvature for conforming to the medial side of the wearer's calf, a second portion having a concave curvature for conforming to the wearer's medial malleolus and subcutaneous bursa, a third portion having a concave curvature for conforming to the wearer's arch.

2. The ankle support of claim 1 wherein the splint has a hinged portion configured to provide rotation for facilitating flexion of the wearer's ankle.

3. The ankle support of claim 1 wherein the splint comprises a cushioning material configured to be oriented towards the wearer.

4. The ankle support of claim 1 wherein the ankle support is ambidextrous.

5. The ankle support of claim 1 wherein the ankle support further comprises an adjustable tension system coupled to the sheet of material.

6. The ankle support of claim 5 wherein the adjustable tension system comprises a tightening mechanism comprising a spool and a cable coupled to the spool and the sheet of material.

7. The ankle support of claim 6 wherein the adjustable tension system further comprises a release mechanism configured to disengage the spool so as to allow rotation of the spool to unwind the cable from the spool and decrease tension in the cable.

8. The ankle support of claim 1 wherein the end of the splint is tapered.

9. The ankle support of claim 1 wherein the splint is in a pocket defined within the sheet of material.

10. The ankle support of claim 1 wherein the splint is in a pocket defined on the outer surface of the sheet of material.

11. The ankle support of claim 1 further comprising a strapping system for securing the splint to the sheet of material, the strapping system comprising one or more straps having hooks at each of its free ends.

12. The ankle support of claim 11 wherein the hooks are configured to engage an adjustable tensioning system such that tightening of the tensioning system tightens the straps.

13. The ankle support of claim 1 further comprising a plurality of straps configured to receive the splint and secure the splint to the sheet of material.

14. A method for securing an ankle support about a wearer's ankle comprising:
positioning a sheet of flexible material at least partially about a portion of a wearer's anatomy, the sheet of material coupled to a splint having an undulating profile; and
securing the sheet of material to the wearer's ankle such that the undulating profile of the splint conforms to at least a portion of the medial side of the wearer's ankle and resists inversion of the ankle by splint providing a generally triangular geometry, wherein there is no splint configured to be positioned on a lateral side of the wearer's ankle when the sheet of material is secured on the wearer's ankle, wherein the undulating profile includes a first portion having a convex curvature for conforming to the medial side of the wearer's calf, a second portion having a concave curvature for conforming to the wearer's medial malleolus and subcutaneous bursa, a third portion having a concave curvature for conforming to the wearer's arch.

15. The method of claim 14 wherein the splint has a hinged portion configured to provide rotation for facilitating flexion of the wearer's ankle.

16. The method of claim 14 wherein tension is applied to the ankle support using an adjustable tension system coupled to the sheet of material.

* * * * *